United States Patent
Lee et al.

(10) Patent No.: US 8,239,009 B2
(45) Date of Patent: Aug. 7, 2012

(54) BIOSIGNAL MEASUREMENT MODULES AND METHODS

(75) Inventors: Wen-Ching Lee, Budai Town (TW); Tsun-Che Huang, Tainan (TW); Chih-Hsiang Ko, Tainan (TW)

(73) Assignee: Industrial Technology Research Institute (TW)

( * ) Notice: Subject to any disclaimer, the term of this patent is extended or adjusted under 35 U.S.C. 154(b) by 609 days.

(21) Appl. No.: 12/421,870

(22) Filed: Apr. 10, 2009

(65) Prior Publication Data

US 2010/0160793 A1   Jun. 24, 2010

(30) Foreign Application Priority Data

Dec. 23, 2008  (TW) .............................. 97150199 A

(51) Int. Cl.
  *A61B 5/02* (2006.01)
(52) U.S. Cl. ........................................ 600/513; 600/485
(58) Field of Classification Search .................. 600/500, 600/513, 526
  See application file for complete search history.

(56) References Cited

U.S. PATENT DOCUMENTS

| | | | |
|---|---|---|---|
| 5,865,755 A | 2/1999 | Golub | |
| 6,120,459 A | 9/2000 | Nitzan et al. | |
| 6,186,953 B1 | 2/2001 | Narimatsu | |
| 6,413,223 B1 | 7/2002 | Yang et al. | |
| 6,599,251 B2 | 7/2003 | Chen et al. | |
| 6,648,828 B2 | 11/2003 | Friedman et al. | |
| 6,872,182 B2 | 3/2005 | Kato et al. | |
| 6,893,401 B2 | 5/2005 | Chen et al. | |
| 2003/0135127 A1* | 7/2003 | Sackner et al. | 600/536 |
| 2005/0261593 A1* | 11/2005 | Zhang et al. | 600/485 |
| 2007/0055163 A1* | 3/2007 | Asada et al. | 600/485 |
| 2007/0142730 A1* | 6/2007 | Laermer et al. | 600/490 |

FOREIGN PATENT DOCUMENTS

| | | |
|---|---|---|
| TW | 389687 | 5/2000 |
| TW | 590761 | 6/2004 |
| TW | M242184 | 9/2004 |
| TW | I268773 | 12/2006 |

* cited by examiner

*Primary Examiner* — Carl H Layno
*Assistant Examiner* — Allen Porter, Jr.
(74) *Attorney, Agent, or Firm* — Lowe Hauptman Ham & Berner, LLP

(57) ABSTRACT

A biosignal measurement module is provided and includes a biosignal measurement unit, a pose detection unit, and a processing unit. The biosignal measurement unit measures an electrocardiogram signal and a pulse signal of a subject. The pose detection unit detects a position of the biosignal measurement module and outputs position signals. The processing unit receives the electrocardiogram signal, the pulse signal, and the position signals. The processing unit generates a height variation parameter, which indicates the height difference between the position of the biosignal measurement module and a reference position, according to the position signals. The processing unit calculates a current pulse transit time according to the electrocardiogram signal and the pulse signal and compensates for the current pulse transit time according to the height variation parameter to obtain a compensated pulse transit time. The processing unit obtains a blood pressure signal according to the compensated pulse transit time.

21 Claims, 4 Drawing Sheets

BIOSIGNAL MEASUREMENT MODULES AND METHODS

RELATED APPLICATIONS

The present application is based on, and claims priority from, Taiwan Application Number 97150199, filed Dec. 23, 2008, the disclosure of which is hereby incorporated by reference herein in its entirety.

BACKGROUND OF THE INVENTION

1. Field of the Invention

The invention relates to a biosignal measurement module, and more particularly to a portable blood-pressure signal measurement module.

2. Description of the Related Art

With aging societies, more and more stress is being placed on hospital resources. Moreover, cardiovascular diseases are increasing, as people age and stress increases for modern day living. For example, people with high blood pressure have increased recently, and is a major cause for apoplexy. Thus, demand for biosignal self-measurement devices has increased so that patients can monitor their own physiology status anytime, to relieve strain on hospital resources and provide needed medical attention to patients.

A conventional blood pressure measurement device applies a wrist-wearing bladder detection unit, which measures blood pressure by filling a bladder with air and bleeding air from the bladder. However, this technique can not continuously measure blood pressure, and it is time consuming to fill the bladder with air and bleed air from the bladder. Furthermore, measuring errors may occur due to height differences between the detected wrist and the heart of the user.

Thus, it is desired to provide a biosignal measurement module which is portable for a patient and can compensate for errors caused by height differences between a detected portion and the heart of a user.

BRIEF SUMMARY OF THE INVENTION

An exemplary embodiment of a biosignal measurement module comprises a biosignal measurement unit, a pose detection unit, and a processing unit. The biosignal measurement unit measures an electrocardiogram signal and a pulse signal of a subject. The pose detection unit detects a position of the biosignal measurement module and outputs a plurality of position signals. The processing unit receives the electrocardiogram signal, the pulse signal, and the position signals. The processing unit generates a height variation parameter, which indicates the height difference between the position of the biosignal measurement module and a reference position, according to the position signals. The processing unit calculates a current pulse transit time according to the electrocardiogram signal and the pulse signal and compensates for the current pulse transit time according to the height variation parameter to obtain a compensated pulse transit time. The processing unit obtains a blood pressure signal according to the compensated pulse transit time.

An exemplary embodiment of a biosignal measurement method comprises the steps of: measuring an electrocardiogram signal and a pulse signal of a subject by a biosignal measurement module; measuring height difference between a position of the biosignal measurement module and a reference position to generate a height variation parameter; calculating a current pulse transit time according to the electrocardiogram signal and the pulse signal; compensating for the current pulse transit time according to the height variation parameter to obtain a compensated pulse transit time; and obtaining a blood pressure signal according to the compensated pulse transit time.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
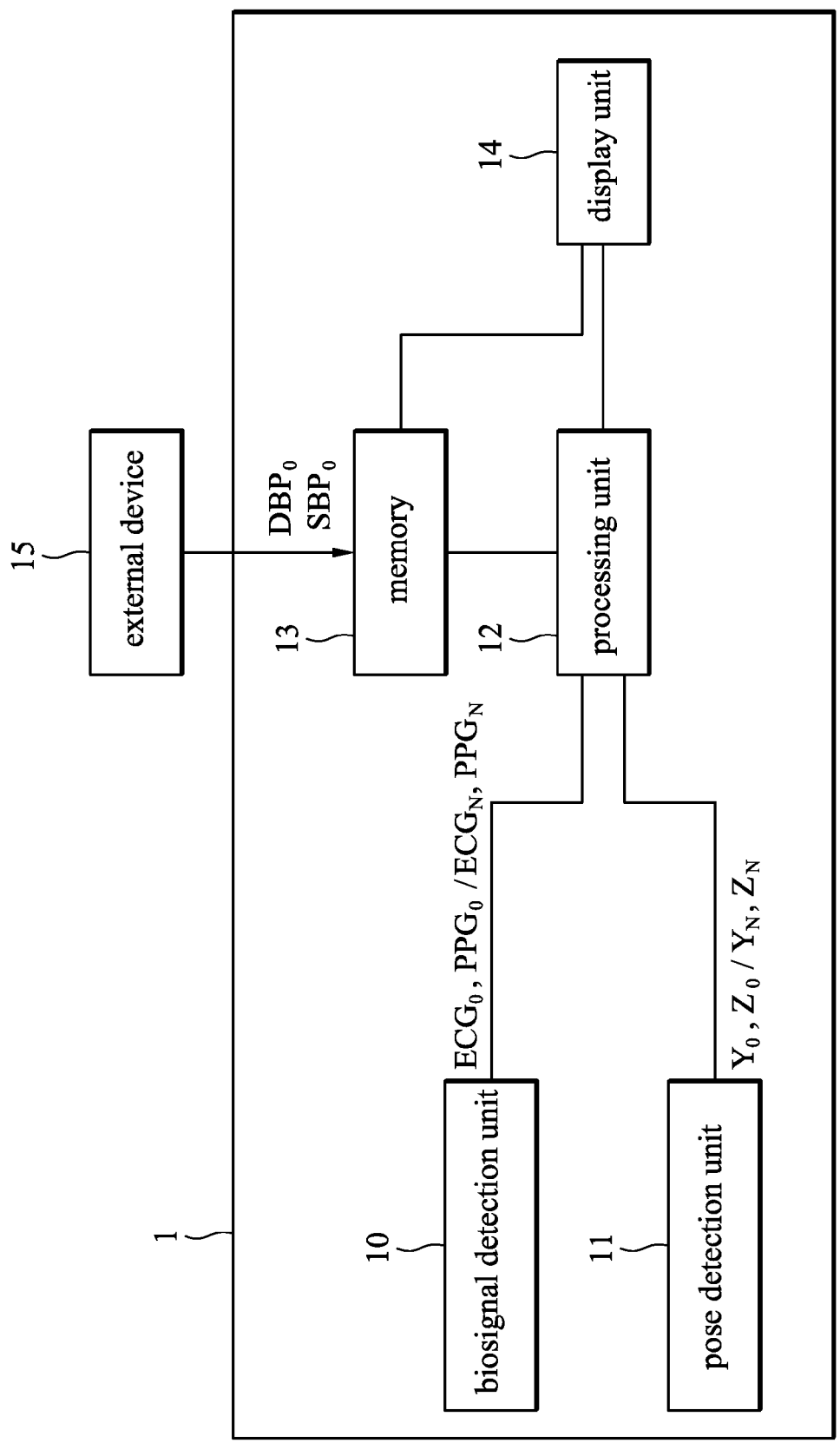
FIG. 1 shows an exemplary embodiment of a biosignal measurement module of the invention.
Figure 2:
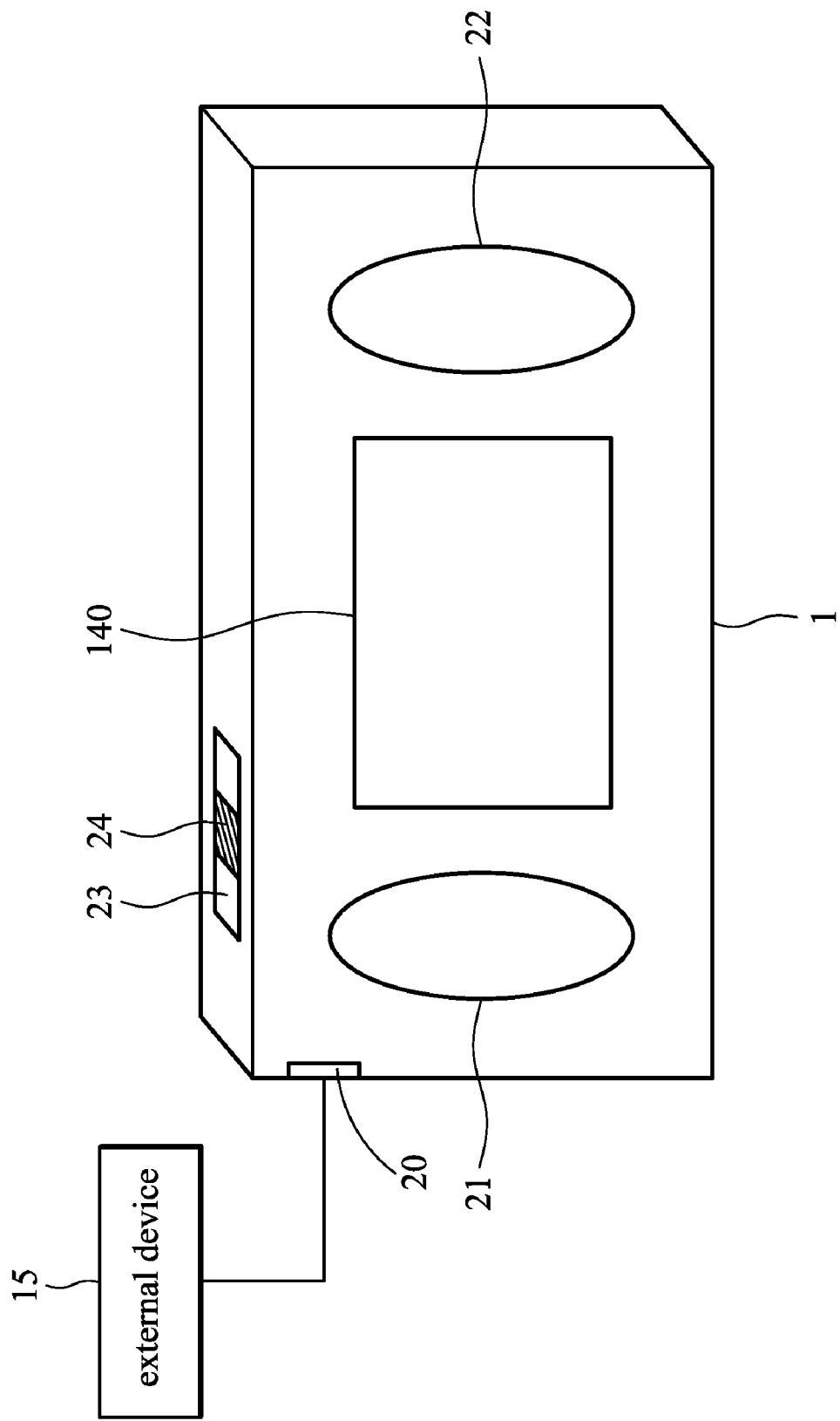
FIG. 2 is a schematic view showing the appearance of the biosignal measurement module of FIG. 1.

Biosignal measurement modules are provided. In an exemplary embodiment of a biosignal measurement module of the invention in FIG. 1, a biosignal measurement module 1 comprises a biosignal detection unit 10, a pose detection unit 11, a processing unit 12, a memory 13, and a display unit 14. FIG. 2 is a schematic view showing the appearance of the biosignal measurement module 1. The biosignal measurement module 1 can operate in an initial parameter setting mode or a measurement mode.

In the initial parameter setting mode, an external device 15 is connected with an input port 20 of the biosignal measurement module 1. The external device 15 can be a known blood pressure meter, such as a digital bladder blood pressure meter. The external device 15 measures, for several seconds, the average diastolic pressure and average systolic pressure of a subject and inputs the measured average diastolic pressure and average systolic pressure to the memory 13 through the input port 20, which serve as an initial diastolic pressure $DBP_0$ and an initial systolic pressure $SBP_0$, respectively.

Figure 3:
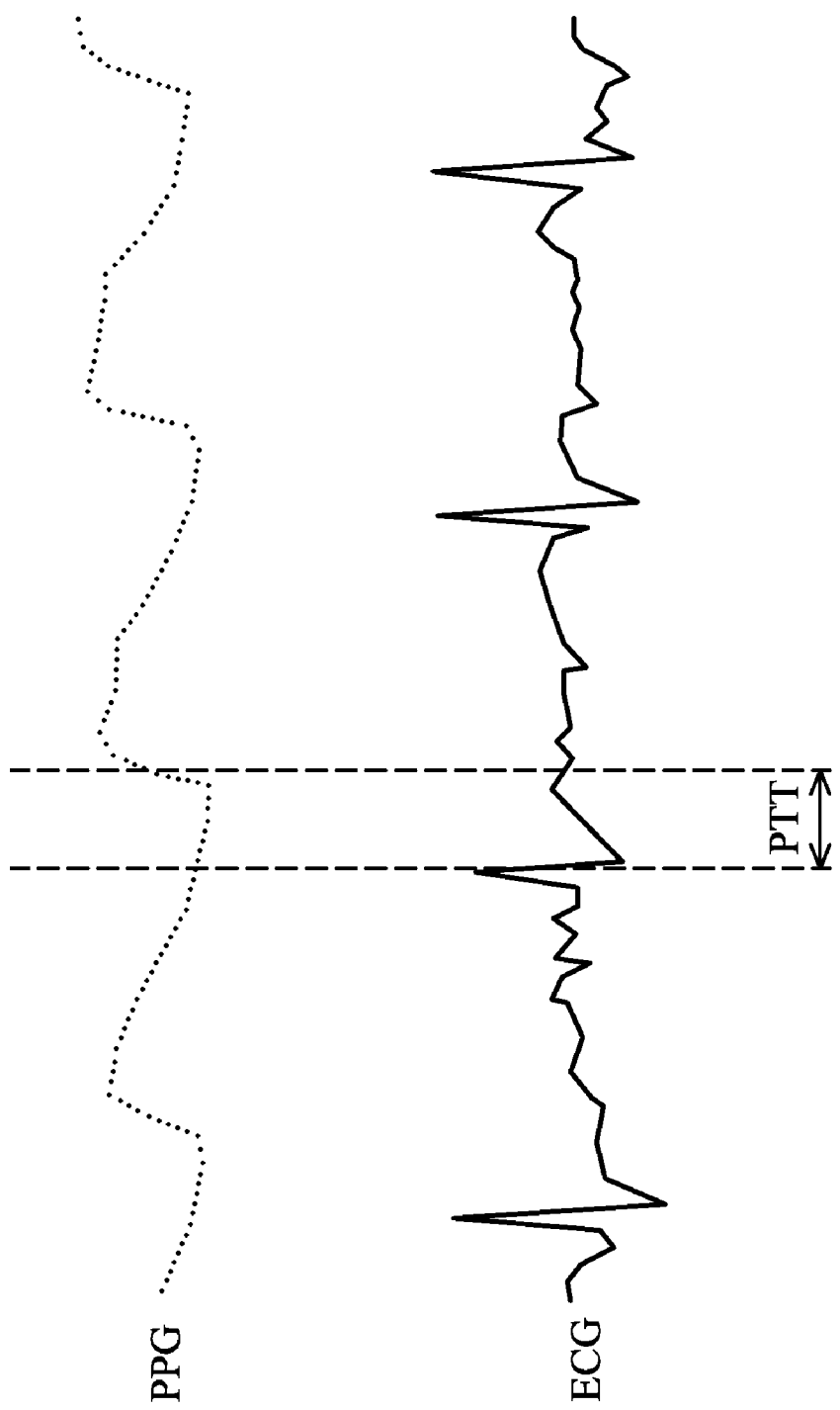
FIG. 3 explains pulse transit time.

Referring to FIG. 2, the biosignal measurement module 1 comprises three detection electrodes 21-23 and one photo detector 24. Three fingers of the subject respectively contact the detection electrodes 21-23 to retrieve an electrocardiogram signal. For example, the forefinger of the left hand of the subject contacts the detection electrode 23, the thumb of the left hand thereof contacts the detection electrode 21, and the thumb of the right hand thereof contacts the detection electrode 22. The photo detector 24 for detecting a pulse signal of the subject can be combined with the detection electrode 23. Thus, the forefinger of the left hand of the subject contacts both of the detection electrode 23 and the photo detector 24. During several seconds of measuring the blood pressure by the external device 15, the biosignal measurement unit 10 of the biosignal measurement module 1 measures an electrocardiogram signal and a pulse signal of the subject with the detection electrodes 21-23 and the photo detector 24, and the measured electrocardiogram signal and the measured pulse signal serve as an initial electrocardiogram signal $ECG_0$ and an initial pulse signal $PPG_0$. The processing unit 12 receives the initial electrocardiogram signal $ECG_0$ and the initial pulse signal $PPG_0$ and calculates a pulse transit time (PTT) according to the initial electrocardiogram signal $ECG_0$ and the initial pulse signal $PPG_0$. Note that for one skilled in the art, it is known that the pulse transit time, is time difference between an electrocardiogram signal ECG and a pulse signal PPG, as shown in FIG. 3. For example, the time difference between the R-wave of the electrocardiogram signal and the time point when the level of the pulse signal starts to rise. In an initial parameter setting mode, the processing unit 12 obtains, during several seconds, a plurality of pulse transit time values and averages the pulse transit time values to obtain an initial pulse transit time $PTT_0$. After the initial pulse transit time $PTT_0$ is obtained, the processing unit 12 calculates a relationship constant K by Equation (1):

$$K = SBP_0 \times PTT_0 \qquad \text{Equation (1)}.$$

According to Equation (1), the relationship constant K relates to the initial systolic pressure $SBP_0$ and the initial pulse transit time $PTT_0$.

When blood pressure is measured for several seconds by the external device 15, the pose detection unit 11 measures an initial height difference $H_0$ between the biosignal measurement module 1 and the heart of the subject. The pose detection unit 11 obtains gravity (G) components in the X axis, Y axis, and Z axis according to the position of the biosignal measurement module 1 to generate corresponding initial position signals; that is, $X_0$, $Y_0$, and $Z_0$ signals. The processing unit 12 calculates the incline angle $\theta_0$ of the lower arm of the subject according to the $Y_0$ signal and the $Z_0$ signal as shown in Equation (2):

$$\theta_0 = \tan^{-1}\left(\frac{Y_0}{Z_0}\right). \qquad \text{Equation (2)}$$

After the incline angle $\theta_0$ is obtained, the processing unit 12 calculates the initial height difference $H_0$ between the biosignal measurement module 1 and the heart of the subject according to Equation (3):

$$H_0 = L_0 - L_1 + L_2 \sin \theta_0 \qquad \text{Equation (3)},$$

wherein $L_0$ represents the height between the heart and the shoulders of the subject, $L_1$ represents the length of the upper arm of the subject, and $L_2$ represent the length of the lower arm of the subject. The subject can input his height by an input unit (not shown) of the biosignal measurement module 1 in advance. The processing unit 12 calculates the values $L_0$, $L_1$, and $L_2$ by applying the height into the standard body proportion equation and stores the obtained values $L_0$, $L_1$, and $L_2$ into the memory 13.

When the processing unit 12 completes the calculation of the initial pulse transit time $PTT_0$, the relationship constant K, and the initial height difference $H_0$, the processing unit 12 transmits the initial parameters to the memory 13 for storage. After the initial parameter setting mode is completed, the memory 13 stores the initial parameters required for individual blood pressure correction comprising the initial diastolic pressure $DBP_0$, the initial systolic pressure $SBP_0$, the initial pulse transit time $PTT_0$, the relationship constant K, and the initial height difference $H_0$. Afterward, the external device 15 can be disconnected with the input port 20.

After the initial parameter setting mode is completed, the biosignal measurement module 1 enters the measurement mode if the subject desires to measure a blood pressure signal. Referring to FIGS. 1 and 2, the same figures of the subject (that is the forefinger and thumb of the left hand and the thumb of the right hand) contact the detection electrodes 21-23, respectively. Simultaneously, the forefinger of the left hand also contacts the photo detector 24. The biosignal measurement unit 10 measures the current electrocardiogram signal $ECG_N$ and the current pulse signal $PPG_N$ through the detection electrodes 21-23 and the photo detector 24 at the same time. The processing unit 12 receives the current electrocardiogram signal $ECG_N$ and the current pulse signal $PPG_N$ and calculates the current pulse transit time $PTT_N$ according to the current electrocardiogram signal $ECG_N$ and the current pulse signal $PPG_N$.

In the measurement mode, the pose detection unit 11 detects the height difference $H_N$ between the biosignal measurement module 1 and the heart of the subject. Similarly, the pose detection unit 11 obtains gravity (G) components in the X axis, Y axis, and Z axis according to the position of the biosignal measurement module 1 to generate corresponding initial position signals; that is $X_N$, $Y_N$, and $Z_N$ signals. The processing unit 12 calculates the incline angle $\theta_N$ of the lower arm of the subject according to the $Y_N$ signal and the $Z_N$ signal as shown in Equation (4):

$$\theta_N = \tan^{-1}\left(\frac{Y_N}{Z_N}\right). \qquad \text{Equation (4)}$$

After the incline angle $\theta_N$ is obtained, the processing unit 12 calculates the height difference $H_N$ between the biosignal measurement module 1 and the heart of the subject according to Equation (5):

$$H_N = L_0 - L_1 + L_2 \sin \theta_N \qquad \text{Equation (5)}.$$

After obtaining the height difference $H_N$ between the biosignal measurement module 1 and the heart of the subject, according to the height difference $H_0$ of the initial parameter setting mode (read from the memory 13) and the height difference $H_N$ of the measurement mode, the processing unit 12 calculates and obtains the height difference $\Delta H$ between the position of the biosignal measurement module 1 in the initial parameter setting mode and that in the measurement mode. The height difference $\Delta H$ serves as a height variation parameter. In other words, the position of the biosignal measurement module 1 in the initial parameter setting mode refers to a reference position, and in the measurement mode, the processing unit 12 calculates the height difference $\Delta H$ (height variation parameter) between the position of the biosignal measurement module and the reference position according to the $Y_N$ signal and the $Z_N$ signal.

After the height variation parameter $\Delta H$ is obtained, the processing unit 12 compensates for the current pulse transit time $PTT_N$ according to the height variation parameter $\Delta H$ to obtain a compensated pulse transit time $PTT_C$, as shown in Equation (6):

$$PTT_C = PTT_N - \left(\frac{\Delta H}{0.54}\right). \qquad \text{Equation (6)}$$

After the compensated pulse transit time $PTT_C$ is obtained, the processing unit 12 reads the relationship constant K obtained in the initial parameter setting mode from the memory 13 and calculates a systolic pressure value $SBP_C$ of the blood pressure signal according to the compensated pulse transit time $PTT_C$ and the relationship constant K, as shown in Equation (7):

$$SBP_C = K[PTT_C]^{-1} \qquad \text{Equation (7)}.$$

After the systolic pressure value $SBP_C$ is obtained, the processing unit 12 reads the initial diastolic pressure $DBP_0$, the initial systolic pressure $SBP_0$, and the initial pulse transit time $PTT_0$ and calculates a diastolic pressure value $DBP_C$ of the blood pressure signal according to the systolic pressure value $SBP_C$, the initial diastolic pressure $DBP_0$, the initial systolic pressure $SBP_0$, the initial pulse transit time $PTT_0$, and the compensated pulse transit time $PTT_C$, as shown in Equation (8):

$$DBP_C = SBP_C - (SBP_0 - DBP_0) \times \left(\frac{PTT_0}{PTT_C}\right)^2. \quad \text{Equation (8)}$$

As described above, in the measurement mode, if the height of the position of the biosignal measurement module 1 diverges from the height of the reference position, the height difference ΔH (height variation parameter) is calculated by the pose detection unit 11. The current pulse transit time $PTT_N$ is then compensated according to the height variation parameter ΔH for precisely calculating the diastolic pressure value and the systolic pressure value, which avoids blood pressure errors caused by the position change of the lower arm of the subject.

According to the above embodiments, it is not necessary for the biosignal measurement module 1 to enter the initial parameter setting mode every time before it enters the measurement mode. When the memory 13 has stored the initial parameters, the subject can measure the blood pressure with the biosignal measurement module 1 at any time. If it is necessary or measurement is required at every predetermined interval, the external device 15 may connected with the biosignal measurement module 1 and the biosignal measurement module 1 enters initial parameter setting mode.

The biosignal measurement module 1 of the embodiment can be integrated in a personal digital assistant (PDA), a mobile phone, a digital camera, a global positioning system, or any other portable electronic equipment.

In the embodiment, the pose detection unit 11 can be implemented by an accelerator, a gyroscope, or a magnetometer. Moreover, the biosignal measurement module 1 further comprises a display unit 14. The display unit 14 can receive the initial diastolic pressure $DBP_0$, the initial systolic pressure $SBP_0$, the initial pulse transit time $PTT_0$, the relationship, and/or the initial height difference $H_0$ from the memory 13. The display unit 14 can also receive the height variation parameter ΔH, the compensated pulse transit time $PTT_C$, the systolic pressure value $SBP_C$, and/or the diastolic pressure value $DBP_C$ which are calculated by the processing unit 12. The display unit 14 shows the subject the received parameters or signals by a display panel 140.

In the embodiment, the photo detector 24 can be combined with one of the detection electrodes 21-23, for example, the photo detector 24 is combined with the detection electrode 23. In other embodiments, the position of the photo detector 24 is close to the position of the detection electrode 23.

Figure 4:
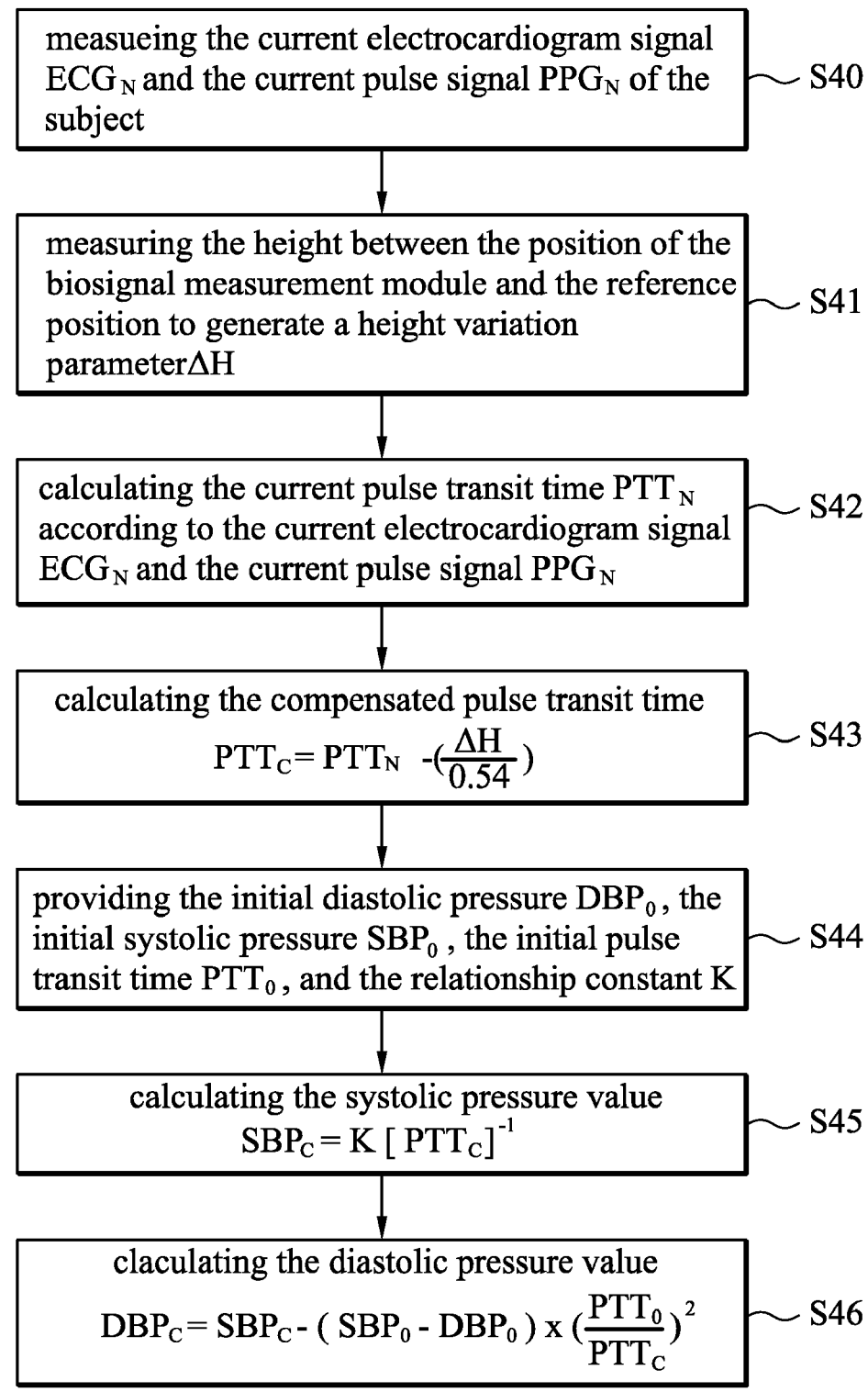
FIG. 4 is a flow chart of an exemplary embodiment of a biosignal measurement method of the invention.

FIG. 4 is a flow chart of an exemplary embodiment of a biosignal measurement method of the invention. Referring to FIGS. 1, 2, and 4, first, the current electrocardiogram signal $ECG_N$ and the current pulse signal $PPG_N$ of the subject are measured by the detection electrodes 21-23 and the photo detector 24 of the biosignal measurement module 1 (step S40). Then, the processing unit 12 measures the height between the position of the biosignal measurement module 1 and the reference position to generate a height variation parameter ΔH (step S41). The processing unit 12 calculates the current pulse transit time $PTT_N$ according to the current electrocardiogram signal $ECG_N$ and the current pulse signal $PPG_N$ (step S42). The processing unit 12 compensates the current pulse transit time $PTT_N$ according to the height variation parameter ΔH to obtain the compensated pulse transit time $PTT_C$, as shown in Equation (6) (step S43). The initial diastolic pressure $DBP_0$ and the initial systolic pressure $SBP_0$ are provided by the external device 15, and the initial pulse transit time $PTT_0$ and the relationship constant K which are stored in advance are provided by the memory 13 (step S44). In the embodiment, the operation of the external device 15 for measuring the initial diastolic pressure $DBP_0$ and the initial systolic pressure $SBP_0$ and the obtainment of the initial pulse transit time $PTT_0$ and the relationship constant K are the same as the above described embodiment of FIG. 1. The processing unit 12 calculates the systolic pressure value $SBP_C$ of the blood pressure signal according to the compensated pulse transit time $PTT_C$ and the relationship constant K, as shown in Equation (7) (step S45). After the systolic pressure value $SBP_C$ is obtained, the processing unit 12 calculates the diastolic pressure value $DBP_C$ of the blood pressure signal according to the systolic pressure value $SBP_C$, the initial diastolic pressure $DBP_0$, the initial systolic pressure $SBP_0$, and the initial pulse transit time $PTT_0$, as shown in Equation (8) (step S46).

In the embodiment of FIG. 4, the step S44 is not limited to follow the step S43. The operation of step S44 must be completed before the step S45.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biosignal measurement module comprising:
a biosignal measurement device comprising detection electrodes for measuring an electrocardiogram signal and a photo detector for detecting a pulse signal of a subject;
a pose detector for detecting a position of the biosignal measurement module and outputting a plurality of position signals; and
a processor, coupled to the biosignal measurement device and the pose detector, configured to:
receive the electrocardiogram signal, the pulse signal, and the position signals;
generate a height variation parameter, which indicates the height difference between the position of the biosignal measurement module and a reference position, according to the position signals;
calculate a current pulse transit time according to the electrocardiogram signal and the pulse signal
compensate for the current pulse transit time according to the height variation parameter to obtain a compensated pulse transit time; and
obtain a blood pressure signal according to the compensated pulse transit time.

2. The biosignal measurement module as claimed in claim 1 further comprising a memory for storing an initial diastolic pressure parameter, an initial systolic pressure parameter, an initial pulse transit time, and a relationship constant, wherein the relationship constant relates to the initial systolic pressure parameter and the initial pulse transit time.

3. The biosignal measurement module as claimed in claim 2, wherein the processor is further configured to calculate a systolic pressure value of the blood pressure signal according to the compensated pulse transit time and the relationship constant.

4. The biosignal measurement module as claimed in claim 3, wherein the processor is further configured to calculate the systolic pressure value according an equation $SBP_C = K[PTTc]^{-1}$, wherein $SBP_C$: represents the systolic pressure value, K represents the relationship constant, and $PTT_C$ represents the compensated pulse transit time.

5. The biosignal measurement module as claimed in claim 4, wherein the relationship constant is obtained by multiplying the initial systolic pressure parameter and the initial pulse transit time.

6. The biosignal measurement module as claimed in claim 3, wherein the processor is further configured to calculate a diastolic pressure value of the blood pressure signal according to the systolic pressure value, the initial systolic pressure parameter, the initial diastolic pressure parameter, the initial pulse transit time, and the compensated pulse transit time.

7. The biosignal measurement module as claimed in claim 6, wherein the processor is further configured to calculate the diastolic pressure value according to an equation $$DBP_C = SBP_C - (SBP_0 - DBP_0) \times \left(\frac{PTT_0}{PTT_C}\right)^2,$$

wherein $DBP_C$ represents the diastolic pressure value, $SBP_C$ represents the systolic pressure value, $SBP_0$ represents the initial systolic pressure parameter, $DBP_0$ represents the initial diastolic pressure parameter, $PTT_0$ represents the initial pulse transit time, and $PTT_C$ represents the compensated pulse transit time.

8. The biosignal measurement module as claimed in claim 2, wherein the initial systolic pressure parameter and the initial diastolic pressure parameter stored in the memory are configured to be provided by an external device.

9. The biosignal measurement module as claimed in claim 8, wherein the external device is configured to measure the initial systolic pressure parameter and the initial diastolic pressure parameter, the biosignal measurement device is configured to measure an initial electrocardiogram signal and an initial pulse of the subject, and the processor is further configured to calculate the initial pulse transit time according to the initial electrocardiogram signal and the initial pulse and to calculate the relationship constant according to the initial systolic pressure parameter and the initial pulse transit time.

10. The biosignal measurement module as claimed in claim 9, wherein the processor is further configured to store the calculated initial pulse transit time and the calculated relationship constant into the memory.

11. The biosignal measurement module as claimed in claim 1, wherein the photo detector is combined with one of the detection electrodes.

12. The biosignal measurement module as claimed in claim 1, wherein the biosignal measurement device is configured to measure the electrocardiogram signal and the pulse signal through at least three fingers of the subject.

13. The biosignal measurement module as claimed in claim 1, wherein biosignal measurement module is integrated in a personal digital assistant (PDA), a mobile phone, a digital camera, a global positioning system, or any other portable electronic equipment.

14. The biosignal measurement module as claimed in claim 1, wherein the processor is further configured to compensate for the current pulse transit time according to an equation $$PTT_C = PTT_N - \left(\frac{\Delta H}{0.54}\right)$$

to obtain the compensated pulse transit time, and $PTT_C$ represents the compensated pulse transit, $PTT_N$ represents the current pulse transit time, and $\Delta H$ represents height variation parameter.

15. A biosignal measurement method comprising:
measuring an electrocardiogram signal and a pulse signal of a subject by a biosignal measurement module;
measuring height difference between a position of the biosignal measurement module and a reference position to generate a height variation parameter;
calculating a current pulse transit time according to the electrocardiogram signal and the pulse signal;
compensating for the current pulse transit time according to the height variation parameter to obtain a compensated pulse transit time;
obtaining a blood pressure signal according to the compensated pulse transit time; and
showing the blood pressure signal on a display unit to indicate blood pressure of the subject.

16. The biosignal measurement method as claimed in claim 15 further comprising providing an initial diastolic pressure parameter, an initial systolic pressure parameter, an initial pulse transit time, and a relationship constant, wherein the relationship constant relates to the initial systolic pressure parameter and the initial pulse transit time.

17. The biosignal measurement method as claimed in claim 16, wherein the step of obtaining the blood pressure signal comprises calculating a systolic pressure value of the blood pressure signal according to the compensated pulse transit time and the relationship constant.

18. The biosignal measurement method as claimed in claim 17, wherein the systolic pressure value is calculated according to an equation $SBP_C = K[PTT_C]^{-1}$, and $SBP_C$ represents the systolic pressure value, $PTT_C$ represents the compensated pulse transit time, K represents the relationship constant which is obtained by $K = SBP_0 \times PTT_0$, $SBP_0$ represents the initial systolic pressure parameter, and $PTT_0$ represents the initial pulse transit time.

19. The biosignal measurement method as claimed in claim 17, wherein the step of obtaining the blood pressure signal further comprises calculating a diastolic pressure value of the blood pressure signal according to the systolic pressure value, the initial systolic pressure parameter, the initial diastolic pressure parameter, the initial pulse transit time, and the compensated pulse transit time.

20. The biosignal measurement method as claimed in claim 19, wherein the diastolic pressure value is calculated according to an equation $$DBP_C = SBP_C - (SBP_0 - DBP_0) \times \left(\frac{PTT_0}{PTT_C}\right)^2,$$

and $DBP_C$ represents the diastolic pressure value, $SBP_C$ represents the systolic pressure value, $SBP_0$ represents the initial systolic pressure parameter, $DBP_0$ represents the initial diastolic pressure parameter, $PTT_0$ represents the initial pulse transit time, and $PTT_C$ represents the compensated pulse transit time.

21. The biosignal measurement method as claimed in claim 15, wherein the current pulse transit time is compensated according to an equation $$PTT_C = PTT_N - \left(\frac{\Delta H}{0.54}\right)$$

and $PTT_C$ represents the compensated pulse transit, $PTT_N$ represents the current pulse transit time, and $\Delta H$ represents height variation parameter.

* * * * *